(12) United States Patent
Utani et al.

(10) Patent No.: US 11,793,681 B2
(45) Date of Patent: Oct. 24, 2023

(54) APPARATUS FOR MANUFACTURING ABSORBENT CORE OF DISPOSABLE WORN ARTICLE, AND REPLACEMENT METHOD FOR REPLACING PART OF THE APPARATUS

(71) Applicant: ZUIKO CORPORATION, Osaka (JP)

(72) Inventors: Kouji Utani, Osaka (JP); Daisuke Furukawa, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 636 days.

(21) Appl. No.: 16/768,134

(22) PCT Filed: Nov. 22, 2018

(86) PCT No.: PCT/JP2018/043140
§ 371 (c)(1),
(2) Date: May 29, 2020

(87) PCT Pub. No.: WO2019/116852
PCT Pub. Date: Jun. 20, 2019

(65) Prior Publication Data
US 2021/0169705 A1    Jun. 10, 2021

(30) Foreign Application Priority Data
Dec. 11, 2017   (JP) ................................. 2017-236737

(51) Int. Cl.
*A61F 13/15*     (2006.01)
*D04H 1/44*      (2006.01)

(52) U.S. Cl.
CPC .. *A61F 13/15642* (2013.01); *A61F 13/15764* (2013.01); *D04H 1/44* (2013.01); *A61F 13/15658* (2013.01); *D10B 2509/026* (2013.01)

(58) Field of Classification Search
None
See application file for complete search history.

(56) References Cited

U.S. PATENT DOCUMENTS

| | | | | |
|---|---|---|---|---|
| 4,666,647 A | * | 5/1987 | Enloe | ........................ B27N 3/14 264/517 |
| 4,995,141 A | | 2/1991 | Gould | |

FOREIGN PATENT DOCUMENTS

| | | |
|---|---|---|
| EP | 3572054 A1 | 11/2019 |
| JP | 2007-044349 A | 2/2007 |

(Continued)

OTHER PUBLICATIONS

International Search Report Issued in PCT/JP2018/043140 dated Feb. 12, 2019.

*Primary Examiner* — Barbara J Musser
(74) *Attorney, Agent, or Firm* — Renner, Otto, Boisselle & Sklar, LLP

(57) ABSTRACT

An apparatus for manufacturing an absorbent core includes: a dispenser for dispensing a fiber; a fiber-stacking drum for stacking the dispensed fiber on the outer circumferential surface while sucking the fiber toward an inside; and a fixed frame for rotatably supporting the fiber-stacking drum. The fiber-stacking drum includes: a rotation shaft; a wheel attached to the distal end of the rotation shaft; and a fiber-stacking ring provided on an outer circumference portion of the wheel for stacking the fiber A suction chamber is fixed to the fixed frame The suction chamber is arranged on an inner side of the fiber-stacking ring and produces a suction force toward an inner circumference of the fiber-stacking ring. The fiber-stacking drum is supported by the fixed frame so as to be slidable in an axial direction of the rotation shaft; and the wheel is removably attached to the distal end of the rotation shaft via a fastener.

6 Claims, 7 Drawing Sheets

(56) References Cited

FOREIGN PATENT DOCUMENTS

| JP | 2007-167509 A | 7/2007 |
|----|---------------|--------|
| JP | 6186543 B1    | 8/2017 |

* cited by examiner

APPARATUS FOR MANUFACTURING ABSORBENT CORE OF DISPOSABLE WORN ARTICLE, AND REPLACEMENT METHOD FOR REPLACING PART OF THE APPARATUS

TECHNICAL FIELD

The present invention relates to an apparatus for manufacturing an absorbent core of a disposable worn article and a method for replacing a part of the apparatus.

BACKGROUND ART

As a method for manufacturing an absorbent core of this type, an absorbent body is typically formed by allowing a crushed fiber to be adsorbed on a fiber-stacking depression formed on the outer circumference of a fiber-stacking drum.

While the fiber-stacking depression of the drum is formed in a predetermined pattern on the outer circumferential surface of a cylindrical fiber-stacking ring, there is a need to change the pattern in accordance with the size of the worn article, for example. The pattern is formed of segments such as a large number of templates and mesh members arranged along the circumferential direction of the drum.

On the other hand, a hood for drawing the fiber onto the drum and a conveyer for introducing a carrier web onto the drum are opposing the outer circumferential surface of the drum.

With the apparatus of the first patent document identified below, the fiber-stacking drum is slidable in the axial direction of the rotation shaft so that the drum can be moved away from the hood and the conveyer. This allows for replacement of segments of the drum such as a large number of templates and mesh members, while preventing interference by the hood and the conveyer.

CITATION LIST

Patent Literature
First Patent Document: U.S. Pat. No. 4,995,141 (front page)

SUMMARY OF INVENTION

With the prior art, however, there is a need to disassemble segments from the drum for replacement. Therefore, for each change of size, there is a need to disassemble a large number of segments and to assemble a large number of other segments. This may lower the facility utilization rate.

It is an object of the present invention to provide an apparatus for manufacturing an absorbent core of a disposable worn article and a method for replacing a part of the apparatus, with which it is possible to improve the facility utilization rate.

The apparatus of the present invention is an apparatus for manufacturing an absorbent core of a disposable worn article, including:
a dispenser 1 for dispensing a crushed fiber;
a fiber-stacking drum 2 for stacking the fiber dispensed from the dispenser 1 on an outer circumferential surface 2f of the drum 2 while sucking the fiber from the outer circumferential surface 2f toward an inside of the drum 2; and
a fixed frame 5 for rotatably supporting the fiber-stacking drum 2, wherein the fiber-stacking drum 2 includes:
a rotation shaft 20 that is rotated;
a wheel 21 attached to one end of the rotation shaft 20; and
a cylindrical fiber-stacking ring 22 provided on an outer circumference portion of the wheel 21 for stacking the fiber, wherein:
a suction chamber 6 is fixed to the fixed frame 5, wherein the suction chamber 6 is arranged on an inner side of the fiber-stacking ring 22 and produces a suction force from an outer circumference toward an inner circumference of the fiber-stacking ring 22;
the fiber-stacking drum 2 is supported by the fixed frame 5 so as to be slidable relative to the fixed frame 5 in an axial direction S, in which an axial line L of the rotation shaft 20 extends; and
the wheel 21 is removably attached to the one end of the rotation shaft 20 via a fastener 23.

The method of the present invention is a replacement method for replacing the wheel 21 and the fiber-stacking ring 22 of the fiber-stacking drum 2 of the manufacturing apparatus, the replacement method including the steps of:
moving the fiber-stacking drum 2 at an operation position P1 to a replacement position P2 away from the dispenser 1 by sliding the fiber-stacking drum 2 in a first direction D1 along the axial line L;
loosening the fastener 23 to remove the wheel 21 and the fiber-stacking ring 22 from the rotation shaft 20;
attaching another wheel 21A and another fiber-stacking ring 22A to the one end. of the rotation shaft 20, in place of the wheel 21 and the fiber-stacking ring 22 having been removed; and
sliding the rotation shaft 20, to which the other wheel 21A and the other fiber-stacking ring 22A have been attached, in a second direction D2, which is opposite to the first direction D1.

According to the present invention, the fiber-stacking ring 22 and the wheel 21 can be replaced without disassembling the fiber-stacking ring 22 into segments. Therefore, the replacement operation can be done in a short amount of time. This, as a result, improves the facility utilization rate.

DESCRIPTION OF EMBODIMENTS

Figure 1:
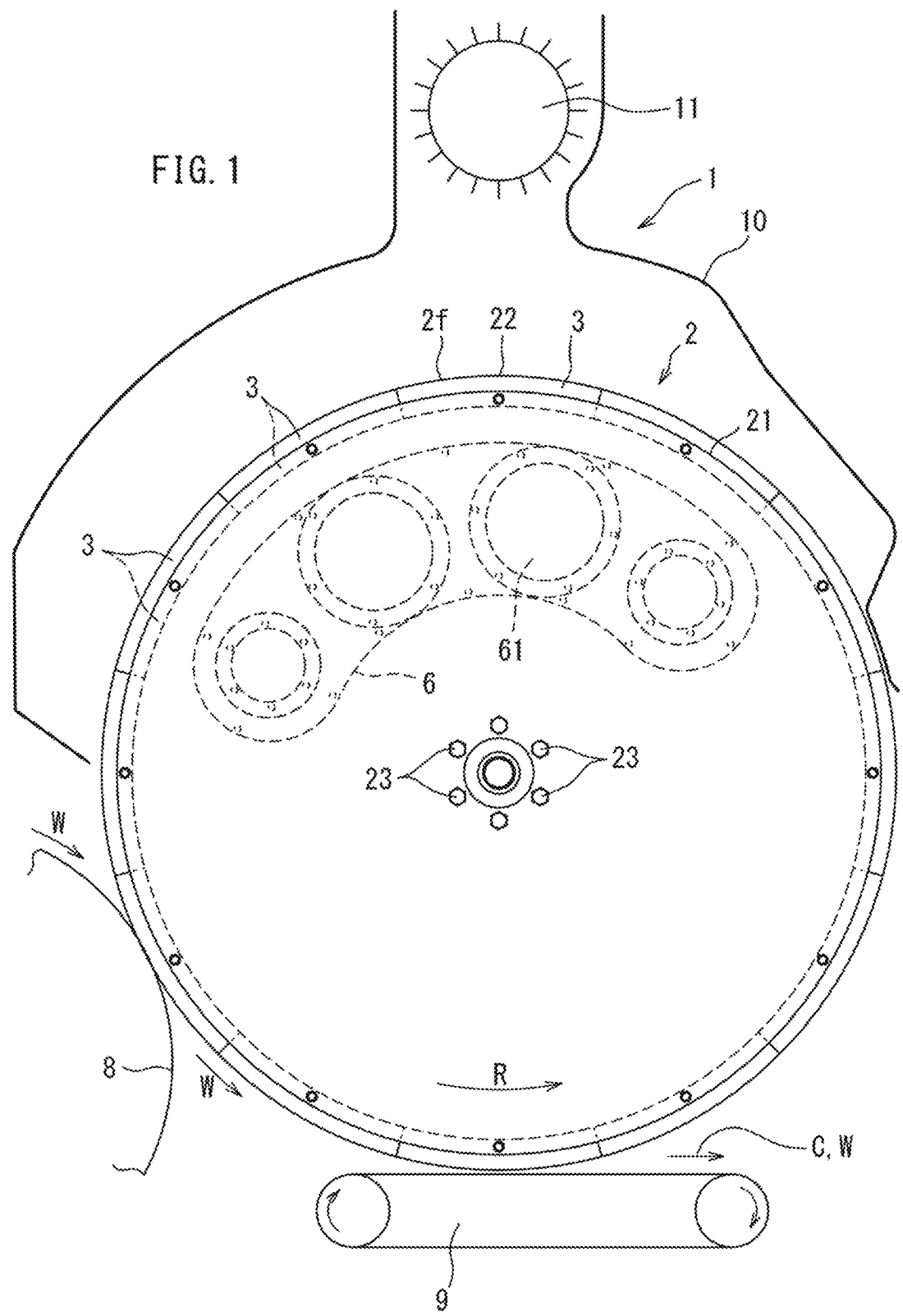
FIG. 1 is a schematic front view of a manufacturing apparatus showing one example of the present invention.

Preferably, with the apparatus of the present invention, the fiber-stacking drum 2 further includes a cylindrical bearing cylinder 24 for rotatably supporting the rotation shaft 20; and the fiber-stacking drum 2 including the bearing cylinder 24 is supported by the fixed frame 5 so as to be slidable relative to the fixed frame 5 in the axial direction S.

In this case, there is no need for a configuration where the rotation shaft 20 can slide in the axial direction S relative to the bearing cylinder 24. Therefore, it is possible with the bearing cylinder 24 to reliably axially support the rotation shaft 20, which rotates at a high speed.

More preferably, an output section M1 of a motor M for rotating the rotation shaft 20 is linked to the other end of the rotation shaft 20; and the motor M, together with the bearing cylinder 24, is supported by the fixed frame 5 so as to be slidable relative to the fixed frame 5 in the axial direction S.

In this case, the replacement can be done while the motor M remains linked to the rotation shaft 20. Thus, it is possible to realize a stable rotation of the motor M and the rotation shaft 20, which rotate at a high speed.

More preferably, the manufacturing apparatus further includes:

a slider 25 fixed to the bearing cylinder 24; and a linear guide 41 for guiding the slider 25 in a direction parallel to the axial direction S.

In this case, it is possible to reliably and easily slide the fiber-stacking drum 2 in the axial direction S.

More preferably, the manufacturing apparatus further includes an actuator 7 for sliding the slider 25 along the linear guide 41.

In this case, it is possible to slide the fiber-stacking drum 2 in the axial direction S by operating the actuator 7.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

One embodiment of the present invention will now be described with reference to the drawings.

An absorbent core to be manufactured by the present manufacturing apparatus is used as the core of incontinence pads as well as disposable pants and diapers, for example, and has an hourglass-like shape, for example.

As shown in FIG. 1, the present manufacturing apparatus includes a dispenser 1, a fiber-stacking drum 2, a suction chamber 6, a guide roll 8 and a conveyer 9.

The dispenser 1 includes a dome-shaped case 10 and a defibrator (a defibration machine) 11. The defibrator 11 defibrates (crushes) a pulp dispensed from upstream into a fibrous material to produce a fluff pulp (fiber). The fluff pulp fills up the case 10, and with the suction chamber 6 of the fiber-stacking drum 2 set at a negative pressure, the fluff pulp is stacked onto the fiber-stacking ring 22 of the fiber-stacking drum 2. Such defibration and fiber-stacking are techniques well known in the art, and are disclosed in JP2009-112438A, for example.

Note that a granular material of a polymer compound having a high absorption capacity called "SAP" (super absorbent polymer particles) may be added as a material of the absorbent core.

Figure 4:
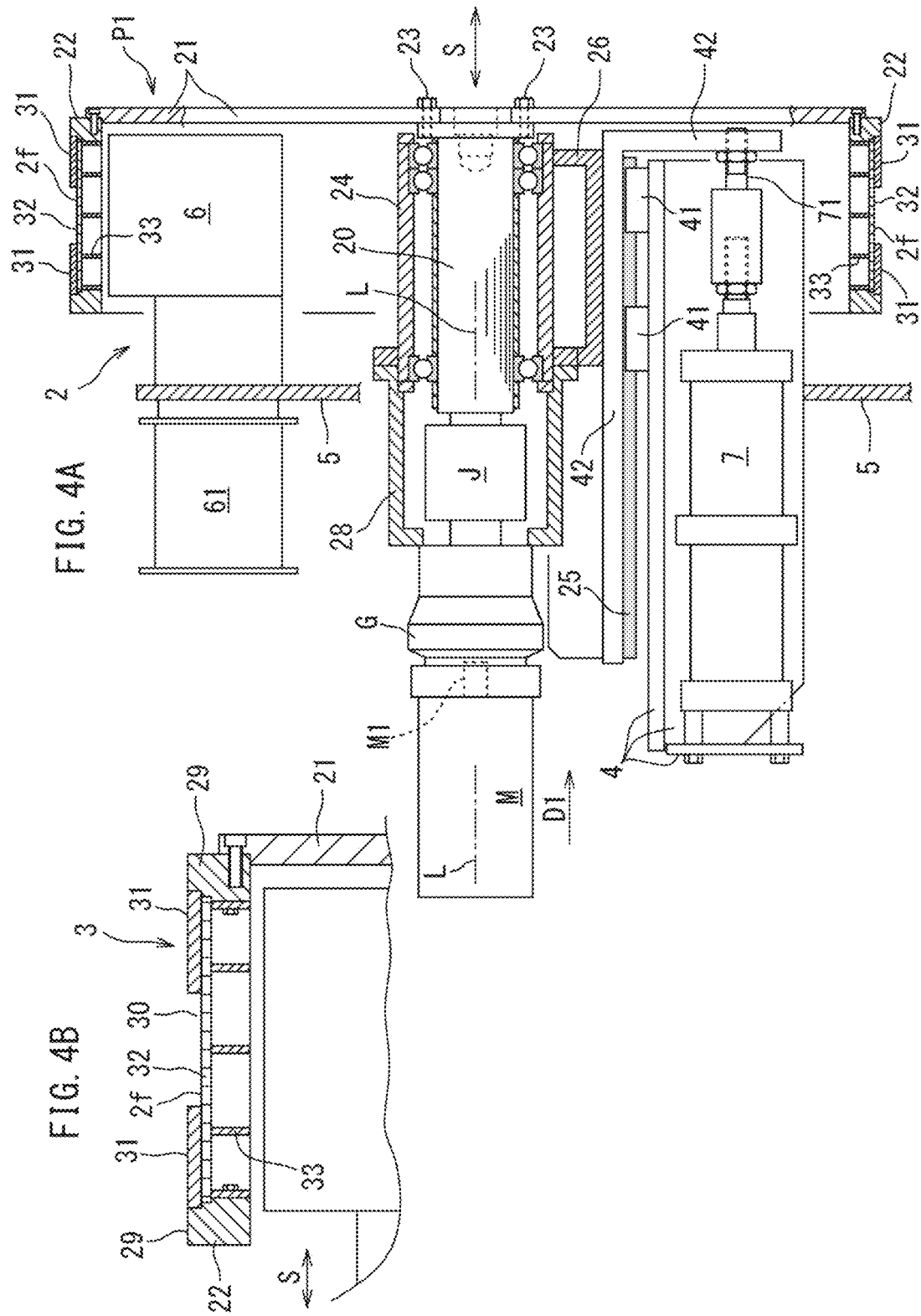
FIG. 4A is a vertical cross-sectional view showing a fiber-stacking drum, etc., while in operation.
FIG. 4B is a cross-sectional view showing the details of a fiber stacking ring.

The fiber-stacking ring 22 of FIG. 4A is generally cylindrical and includes a plurality of, or a large number of, segments 3 arranged along the circumferential direction R of FIG. 1.

Figure 2:
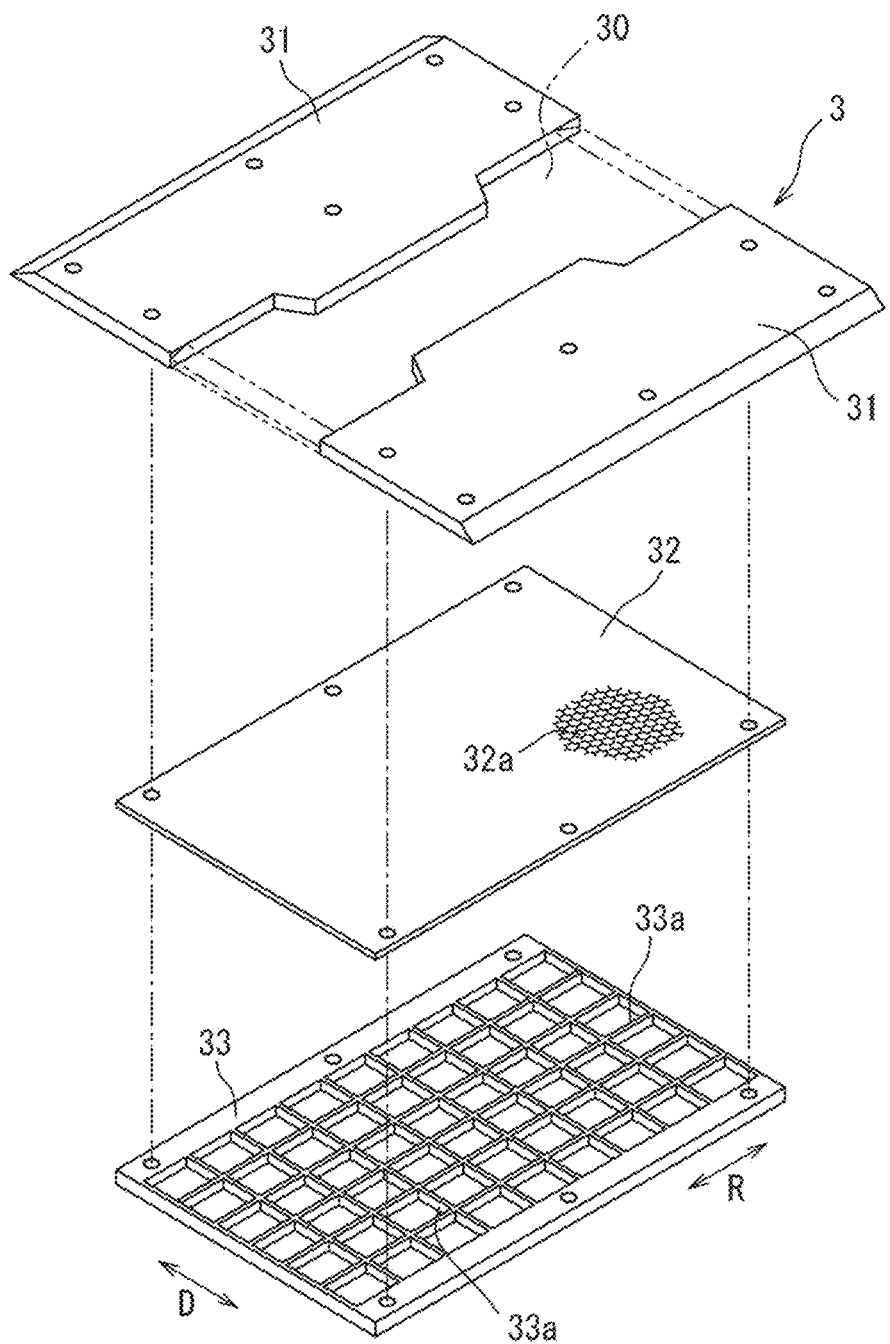
FIG. 2 is a perspective view showing a segment disassembled.

For the sake of illustration, FIG. 2 shows components of one segment 3 disassembled and arranged in a flat layout. Each segment 3 includes a template 31, a mesh member 32 and a lattice member 33, etc.

A large number of, or countless, through holes 32a are formed in the mesh member 32 by performing an etching process well known in the art on a thin metal plate. The through holes 32a are sized so that they allow air therethrough but can receive the fiber and SAP. For example, a pair of templates 31 are provided and arranged on the outer circumferential surface side of the mesh member 32, forming a fiber-stacking depression 30.

Note that for the sake of illustration, meshes of the mesh member 32 are shown enlarged and only some of them are shown.

The pair of templates 31 and 31 are spaced apart from each other in the width direction D, wherein the space therebetween forms the fiber-stacking depression 30. The fiber stacked in the fiber-stacking depression 30 becomes an absorbent core of an individual worn article.

That is, the fiber-stacking drum 2 of FIG. 1, while continuously rotating in the circumferential direction R, sucks the fiber dispensed from the dispenser 1 toward the suction chamber 6 on the inner side from an outer circumferential surface 2f (FIG. 4A) of the fiber-stacking ring 22, thereby continuously stacking the fiber onto the outer circumferential surface 2f of a predetermined fiber-stacking depression 30 of FIG. 4B. That is, the fiber is stacked on the outer circumferential surface 2f of the cylindrical fiber-stacking ring 22 defining the fiber-stacking depression 30.

The lattice member 33 of FIG. 2 is formed of frames 33a extending in the width direction. D and the circumferential direction R so as not to inhibit suction of the fiber. The lattice member 33 is in contact with the mesh member 32 and supports the inner circumferential surface of the mesh member 32, which is vulnerable to an external force.

Figure 3:
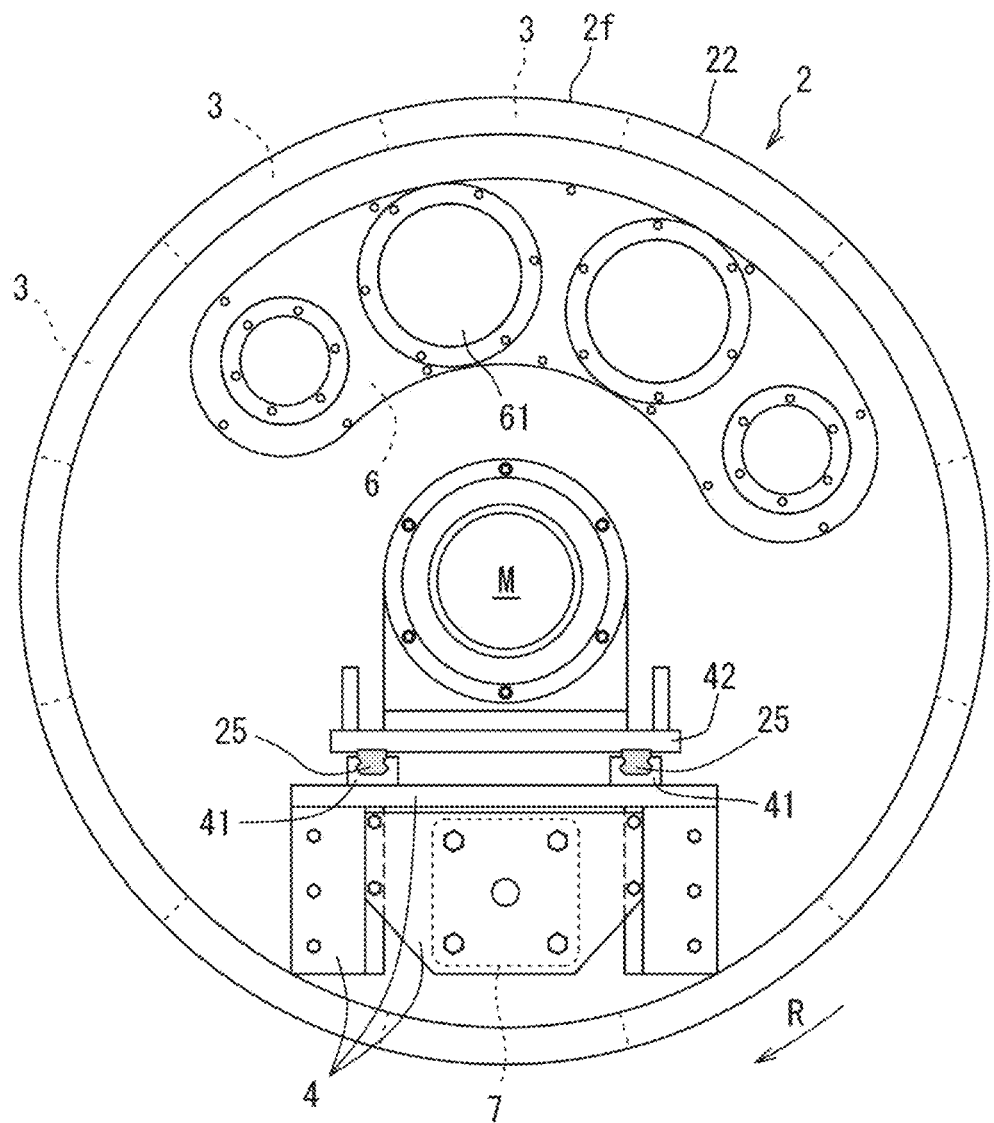
FIG. 3 is a schematic back view of the manufacturing apparatus.

As shown in FIG. 3, the suction chamber 6 is arranged over a predetermined section of the fiber-stacking drum 2 in the circumferential direction R, and is connected to a negative pressure source (not shown) via a plurality of ducts 61 so that the inside of the chamber is at a negative pressure.

As shown in FIG. 4A, the suction chamber 6 is arranged close to the inner circumference side of the fiber-stacking ring 22 of the fiber-stacking drum 2. That is, the suction chamber 6 is fixed to the fixed frame 5, wherein the suction chamber 6 is in contact with the inner circumference of (arranged on the inner side of) the fiber-stacking ring 22 and produces a suction force exerting from the outer circumference of the fiber-stacking ring 22 toward the inner circumference of the fiber-stacking ring 22. For example, this suction chamber 6 may be fixed to the fixed frame 5 via the ducts 61.

The fixed frame 5 is a vertical place well known in the art that supports the various machine parts of the apparatus for manufacturing a disposable worn article. As will be described below, the fixed frame 5 rotatably supports the fiber-stacking drum 2.

As shown in FIG. 4A, the fiber-stacking drum 2 includes a rotation shaft 20 that is rotated, a wheel 21 attached to the distal end (one end) of the rotation shaft 20, and the cylindrical fiber-stacking ring 22.

The fiber-stacking ring 22 is provided on the outer circumference portion along the edge of the wheel 21 for stacking the fiber. The wheel 21 is removably attached to the distal end (one end) of the rotation shaft 20 via a fastener 23. For example, the fastener 23 may include a plurality of bolts, which pass through the wheel 21 and are screwed into the distal end of the rotation shaft 20.

As shown in FIG. 4A and FIG. 4B, the fiber-stacking ring 22 includes a pair of annular frame rings 29. A large number of segments 3 are arranged next to each other in the circumferential direction R as shown in FIG. 1 along the annular frame rings 29.

As shown in FIG. 4B, the pair of frame rings 29, 29 are linked to each other in the axial direction S via the lattice member 33. The template 31, the mesh member 32 and the lattice member 33 of each segment 3 are fixed between the pair of frame rings 29, 29 in the axial direction S.

As shown in FIG. 4A, the fiber-stacking drum 2 further includes a cylindrical bearing cylinder (a cylindrical bearing sleeve) 24 that rotatably supports the rotation shaft 20. An output section of a servomotor M that rotates the rotation shaft 20 is linked to the proximal end (the other end) of the rotation shaft 20 via a decelerator G and a coupling J. The motor M is fixed to the bearing cylinder 24 via the decelerator G.

A link portion 26 is attached to the bearing cylinder 24, and a case 28 extending in the axial direction S is attached to one end of the link portion 26. A portion of the rotation shaft 20 and the coupling J are accommodated inside the case 28, and the opening of the case 28 is covered (lidded) by the decelerator G. That is, the rotation shaft 20 and the coupling J are accommodated in the space that is formed by the bearing cylinder 24, the case 28 and the decelerator G, and it is therefore possible to prevent the crushed fluff pulp (fiber) from being stuck on the rotation shaft 20, etc.

The bearing cylinder 24 is fixed to a slider 25. That is, the slider 25 is attached to the bearing cylinder 24 via the link portion 26 and a moving plate 42. The slider 25 is guided by a linear guide 41 in the direction parallel to the axial direction S. The linear guide 41 is fixed to the fixed frame 5 via a base 4. Note that the slider 25 is colored in gray in the figures.

An actuator 7 such as an air cylinder is attached to the base 4. That is, the actuator 7 is fixed to the fixed frame 5 via the base 4. In other words, the actuator 7 is attached to a non-rotating portion of the present manufacturing apparatus.

The actuator 7 slides the motor M, the bearing cylinder 24 and the fiber-stacking drum 2 in the axial direction S via the slider 25, the moving plate 42 and the link portion 26.

Figure 5:
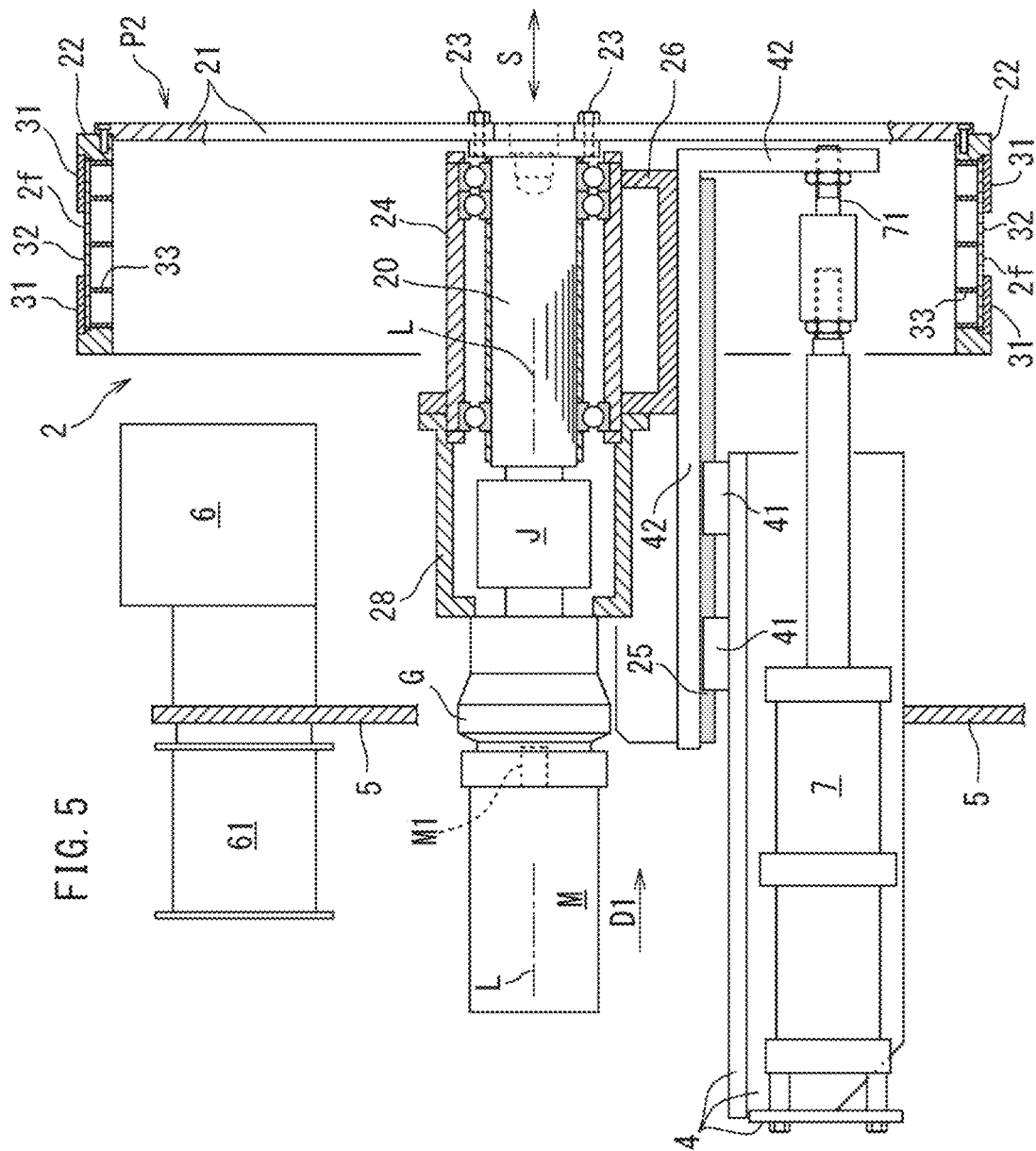
FIG. 5 is a vertical cross-sectional view showing the fiber stacking drum, etc., during replacement.

For example, the moving plate 42 is fixed to the distal end of a rod 71 of an air cylinder 7, and the fiber-stacking drum 2 slides between the operation position P1 of FIG. 4A and the replacement position P2 of FIG. 5.

Thus, the fiber-stacking drum 2, together with the motor M and the bearing cylinder 24, is supported by the fixed frame 5 so as to be slidable relative to the fixed frame 5 in the axial direction S, in which the axial line L of the rotation shaft 20 extends.

In the present embodiment, since the axial line L of the rotation shaft 20 and the axial line L of the motor M are arranged on the same axial line, the bearing cylinder 24, the motor M and the fiber-stacking drum 2 can easily slide in the axial direction S.

Next, a method for manufacturing an absorbent core will be described briefly.

While manufacturing an absorbent core, the fiber-stacking drum 2 is set to the operation position P1 of FIG. 4A.

A carrier web W is continuously introduced from the guide roll 8 onto the fiber-stacking drum 2 of FIG. 1. On the other hand, while the fiber-stacking drum 2 continuously rotates in the circumferential direction R, the fiber dispensed from the dispenser 1 is sucked by the suction chamber 6 toward the inside from the outer circumferential surface $2f$ of the fiber-stacking drum 2 (the outer circumferential surface $2f$ of the fiber-stacking depression 30). Thus, the fiber is continuously stacked on the outer circumferential surface $2f$ (FIG. 4B) of the fiber-stacking depression 30, thereby producing a continuous core C.

In FIG. 1, as well known in the art, the carrier web W dispensed from the guide roll 8 is laid over the stacked continuous core C. Then, the continuous core C and the carrier web W are rolled out of the fiber-stacking drum 2 as an integral material. Then, as well known in the art, it may be severed into absorbent cores of individual worn articles on the downstream side (not shown). Instead of producing the continuous core C, individual absorbent cores may be produced by fiber-stacking on the fiber-stacking drum 2.

Next, a replacement method for replacing the wheel 21 and the fiber-stacking ring 22 of the fiber-stacking drum 2 of the manufacturing apparatus.

In order to replace, first, the operator slides the fiber-stacking drum 2 of FIG. 4A from the operation position P1 to the replacement position P2 of FIG. 5. That is, the wheel 21 and the fiber-stacking ring 22 are moved from the operation position P1 to the replacement position P2 of FIG. 5 by sliding the motor M, the bearing cylinder 24 and the fiber-stacking drum 2 in the first direction D1 along the axial line L by protruding the rod 71 of the air cylinder 7 of FIG. 4A. Thus, the wheel 21 and the fiber-stacking ring 22 move to a position away from the dispenser 1 (FIG. 1).

Note that the first direction D1 means the direction from the proximal end (the proximal end of the rotation shaft 20) to which the output section M1 of the motor M is linked toward one end (one end of the rotation shaft 20) to which the wheel 21 is attached.

Figure 6:
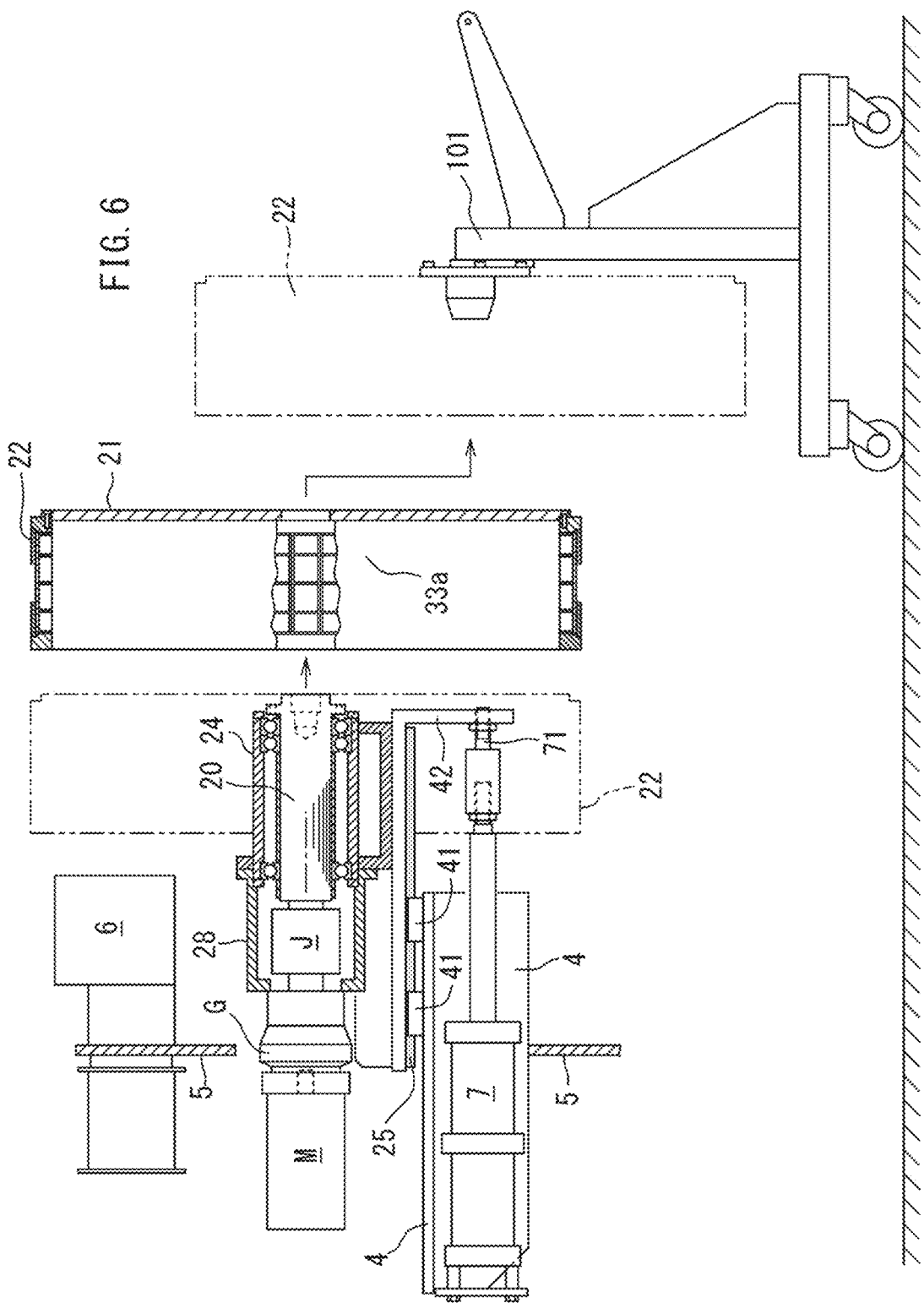
FIG. 6 is a schematic side view showing a method for removing a fiber stacking ring.

Then, the operator loosens the fastener 23 of FIG. 5 and removes the wheel 21 and the fiber-stacking ring 22 from the rotation shaft 20. As shown in FIG. 6, the wheel 21 and the fiber-stacking ring 22 having been removed are moved onto a first platform truck 101.

Figure 7:
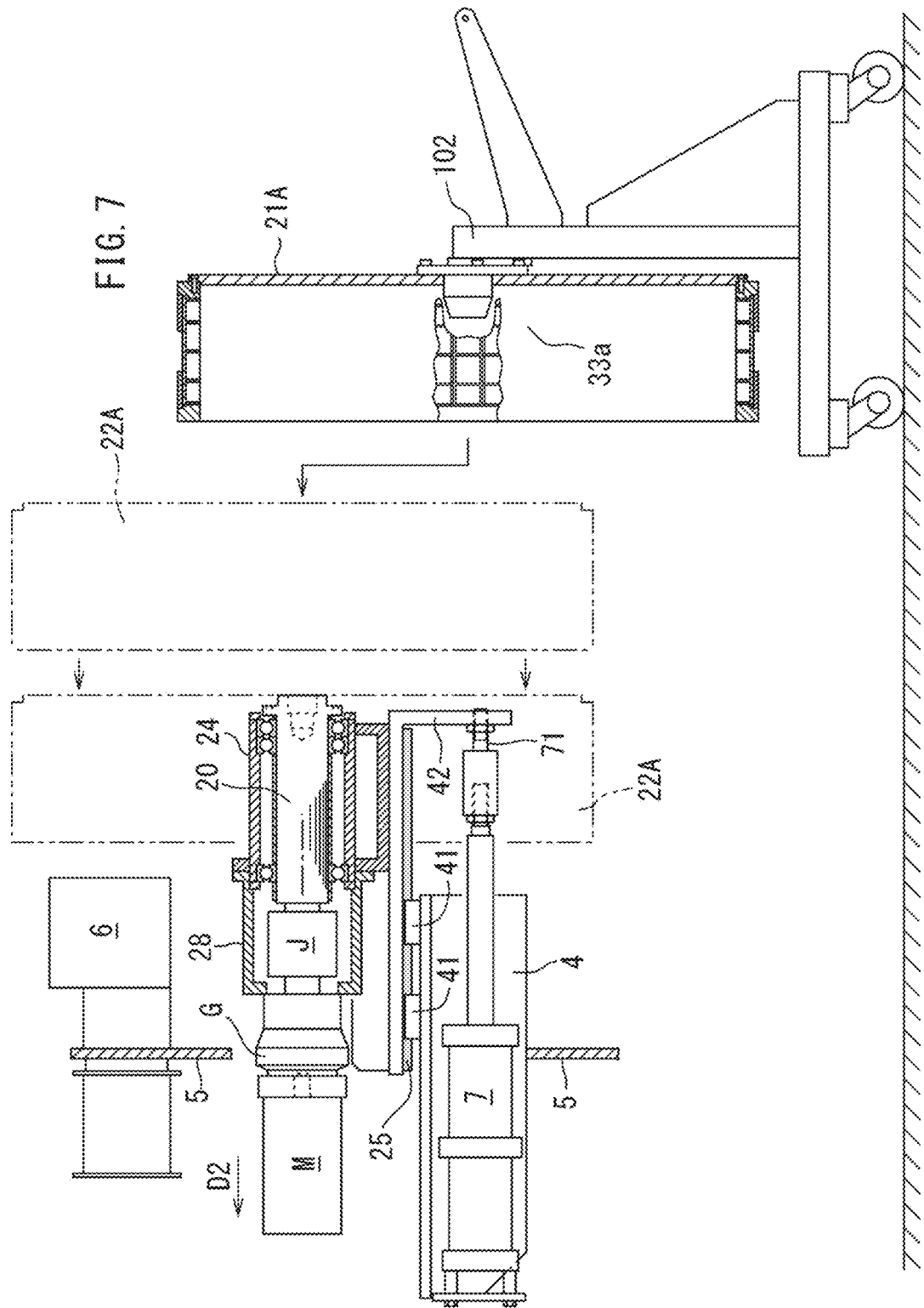
FIG. 7 is a schematic side view showing a method for installing a fiber-stacking ring.
Note that sliders and bearing inner and outer races are colored in gray for ease of understanding of the drawings.

The operator moves another wheel (a substitute wheel) 21A and another fiber-stacking ring (a substitute fiber-stacking ring) 22A of FIG. 7 from a second platform truck 102 and attaches them to the distal end of the rotation shaft; 20, in place of the wheel 21 and the fiber-stacking ring 22 of FIG. 6 having been removed. The segments 3 on the other fiber-stacking ring 22A may be of a different pattern from the segments of the removed fiber-stacking ring 22.

Thereafter, through an opposite procedure from the removal, the operator actuates the actuator 7 to slide the rotation shaft 20, to which the other wheel 21A and the other fiber-stacking ring 22A have been attached, together with the motor M and the bearing cylinder 24 of FIG. 5, in the second direction D2, which is opposite to the first direction D1.

Thus, replacement can be done quickly when manufacturing worn articles of different sizes, for example.

While one embodiment has been described above with reference to the drawings, obvious variations and modifications will readily occur to those skilled in the art upon reading the present specification.

For example, the replacement of the wheel and the fiber-stacking ring may be done for a change in the shape of the absorbent core, instead of a change in size.

When replacing the fiber-stacking ring, only segments may be replaced without replacing the wheel.

A plurality of through holes may be provided in the wheel for reducing the weight thereof.

Thus, such variations and modifications shall fall within the scope of the present invention as defined by the appended claims.

INDUSTRIAL APPLICABILITY

The present invention is applicable to an apparatus for manufacturing an absorbent core of a disposable worn article,

REFERENCE SIGNS LIST

1 Dispenser,
10: Case,
11: Defibrator
2: Fiber-stacking drum,
2f: Outer circumferential surface,
20: Rotation shaft,
21: Wheel
22: Fiber-stacking ring,
29: Frame ring
21A: Another wheel,
22A: Another fiber-stacking ring
23: Fastener,
24: Bearing cylinder,
25: Slider,
26: Link portion,
28: Case
3: Segment,
30: Fiber-stacking depression,
31: Template,
32: Mesh member
32f: Inner circumferential surface side,
33: Lattice member,
33a: Frame
4: Base,
41: Linear guide,
42: Moving plate
5: Fixed frame,
6: Suction chamber,
61: Duct
7: Actuator,
71: Rod,
8: Guide roll,
9: Conveyer
101, 102: Platform truck.
C: Continuous core,
L: Axial line,
S: Axial direction
M: Motor,
M1: Output section,
G: Decelerator,
J: Coupling
P1: Operation position,
P2: Replacement position.
R: Circumferential direction,
D: Width direction,
D1: First direction,
D2: Second direction
W: Carrier web

The invention claimed is:

1. An apparatus for manufacturing an absorbent core of a disposable worn article, comprising:
a dispenser for dispensing a crushed fiber;
a fiber-stacking drum for stacking the fiber dispensed from the dispenser on an outer circumferential surface while sucking the fiber from the outer circumferential surface toward an inside; and
a fixed frame for rotatably supporting the fiber-stacking drum, wherein the fiber-stacking drum includes:
a rotation shaft that is rotated;
a wheel attached to one end of the rotation shaft ; and
a cylindrical fiber-stacking ring provided on an outer circumference portion of the wheel for stacking the fiber, wherein:
a suction chamber is fixed to the fixed frame, wherein the suction chamber is arranged on an inner side of the fiber-stacking ring and produces a suction force from an outer circumference toward an inner circumference of the fiber-stacking ring;
the fiber-stacking drum is supported by the fixed frame so as to be slidable relative to the fixed frame in an axial direction, in which an axial line of the rotation shaft extends; and
the wheel is removably attached to the one end of the rotation shaft via a fastener,
the fiber-stacking drum further includes a cylindrical bearing cylinder for rotatably supporting the rotation shaft; and
the fiber-stacking drum including the bearing cylinder is supported by the fixed frame so as to be slidable relative to the fixed frame in the axial direction,
an output section of a motor for rotating the rotation shaft is linked to another end of the rotation shaft; and
the motor, together with the bearing cylinder, is supported by the fixed frame so as to be slidable relative to the fixed frame in the axial direction.

2. The manufacturing apparatus according to claim 1, further comprising:
a slider fixed to the bearing cylinder; and
a linear guide for guiding the slider in a direction parallel to the axial direction.

3. The manufacturing apparatus according to claim 2, further comprising an actuator for sliding the slider along the linear guide.

4. The manufacturing apparatus according to claim 1, wherein:
the fiber-stacking drum further includes a cylindrical bearing cylinder for rotatably supporting the rotation shaft;
an output section of a motor for rotating the rotation shaft is linked to another end of the rotation shaft;
the motor is fixed to the bearing cylinder;
a slider is attached to the bearing cylinder;
a linear guide is fixed to the fixed frame, the linear guide guiding the slider in a direction parallel to the axial direction; and
an actuator is fixed to the fixed frame, the actuator sliding the fiber-stacking drum including the bearing cylinder and the motor in the axial direction via the slider.

5. A replacement method for replacing the wheel and the fiber-stacking ring of the fiber-stacking drum of the manufacturing apparatus of claim 1, the replacement method comprising the steps of:

moving the fiber-stacking drum at an operation position to a replacement position away from the dispenser by sliding the fiber-stacking drum in a first direction along the axial line;

loosening the fastener to remove the wheel and the fiber-stacking ring from the rotation shaft;

attaching another wheel and another fiber-stacking ring to the one end of the rotation shaft, in place of the wheel and the fiber-stacking ring having been removed; and sliding the rotation shaft, to which the other wheel and the other fiber-stacking ring have been attached, in a second direction, which is opposite to the first direction.

6. A replacement method for replacing the wheel and the fiber-stacking ring of the fiber-stacking drum of the manufacturing apparatus of claim 4, the replacement method comprising the steps of:

actuating the actuator to slide the motor, the bearing cylinder and the fiber-stacking drum at an operation position in a first direction along the axial line so as to move the fiber-stacking ring to a replacement position away from the dispenser;

loosening the fastener to remove the wheel and the fiber-stacking ring from the rotation shaft;

attaching another wheel and another fiber-stacking ring to the one end of the rotation shaft, in place of the wheel and the fiber-stacking ring having been removed; and actuating the actuator to slide the rotation shaft, to which the other wheel and the other fiber-stacking ring have been attached, together with the motor and the bearing cylinder, in a second direction, which is opposite to the first direction.

* * * * *